(12) United States Patent
Kakinuma et al.

(10) Patent No.: US 9,096,506 B2
(45) Date of Patent: Aug. 4, 2015

(54) 1,1-BIS[(ETHENYLOXY)METHYL]-CYCLOHEXANE AND METHOD OF PRODUCTION OF SAME

(75) Inventors: Shinichi Kakinuma, Kanagawa (JP); Masahiro Murotani, Kanagawa (JP); Seijin Nakamori, Kanagawa (JP)

(73) Assignee: NIPPON CARBIDE INDUSTRIES CO., INC., Tokyo (JP)

( * ) Notice: Subject to any disclaimer, the term of this patent is extended or adjusted under 35 U.S.C. 154(b) by 309 days.

(21) Appl. No.: 13/643,931

(22) PCT Filed: Apr. 28, 2011

(86) PCT No.: PCT/JP2011/060433
§ 371 (c)(1),
(2), (4) Date: Oct. 26, 2012

(87) PCT Pub. No.: WO2011/136355
PCT Pub. Date: Nov. 3, 2011

(65) Prior Publication Data
US 2013/0041184 A1    Feb. 14, 2013

(30) Foreign Application Priority Data
Apr. 28, 2010  (JP) .................................. 2010-103711

(51) Int. Cl.
| C07C 41/06 | (2006.01) |
| C07C 43/188 | (2006.01) |
| C07C 41/03 | (2006.01) |
| C07C 43/162 | (2006.01) |

(52) U.S. Cl.
CPC ............... *C07C 41/03* (2013.01); *C07C 43/162* (2013.01)

(58) Field of Classification Search
CPC .................................................. C07C 43/162
USPC ........................................................ 568/670
See application file for complete search history.

(56) References Cited

U.S. PATENT DOCUMENTS

| 6,306,923 B1 * | 10/2001 | Thepot et al. ............... 522/107 |
| 2003/0144442 A1 | 7/2003 | Gross et al. |
| 2003/0144443 A1 | 7/2003 | Gross et al. |
| 2003/0144444 A1 | 7/2003 | Gross et al. |
| 2003/0144445 A1 | 7/2003 | Gross et al. |
| 2009/0198014 A1 | 8/2009 | Baikerikar et al. |
| 2012/0083628 A1 | 4/2012 | Kakinuma et al. |

FOREIGN PATENT DOCUMENTS

| GB | 838020 | * 10/1956 |
| JP | 2001-278829 A | 10/2001 |
| JP | 2002-544306 A | 12/2002 |
| JP | 2003-327686 | 11/2003 |
| JP | 2009-101326 A | 5/2009 |
| JP | 2009-525382 A | 7/2009 |
| WO | WO-00/68297 A1 | 11/2000 |
| WO | WO-2005/005456 A2 | 1/2005 |
| WO | WO-2007/092071 A1 | 8/2007 |
| WO | WO-2010/137742 A1 | 12/2010 |

OTHER PUBLICATIONS

International Search Report mailed Aug. 2, 2011.

* cited by examiner

*Primary Examiner* — Rosalynd Keys
(74) *Attorney, Agent, or Firm* — Fishman Stewart Yamaguchi PLLC

(57) ABSTRACT

A novel compound, 1,1-bis[(ethenyloxy)methyl]cyclohexane having the formula (I) and having a low odor, low volatility and low skin irritability, which is useful as a starting material for a polymerization composition having a low toxicity and excellent curability, adhesiveness and transparency in the ultraviolet light region, and having a special reactivity alone or with another compound, and a method for producing the same:

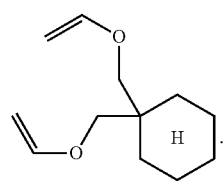

(I)

5 Claims, 2 Drawing Sheets

1,1-BIS[(ETHENYLOXY)METHYL]-CYCLOHEXANE AND METHOD OF PRODUCTION OF SAME

TECHNICAL FIELD

The present invention relates to a novel vinyl ether, 1,1-bis[(ethenyloxy)methyl]cyclohexane, and a method of production of the same.

BACKGROUND ART

The 1,1-bis[(ethenyloxy)methyl]cyclohexane according to the present invention (another name: 1,1-cyclohexanedimethanol divinylether) has never been reported in the past and is considered to be a novel compound.

SUMMARY OF INVENTION

Technical Problem

An object of the present invention is to provide 1,1-bis[(ethenyloxy)methyl]cyclohexane having a low odor, low volatility, low skin irritability, and low toxicity and useful as a starting material for a polymerization composition having an excellent curability, adhesiveness, transparency in the ultraviolet light region, etc. and a method for producing the same. The 1,1-bis[(ethenyloxy)methyl]cyclohexane of the present invention is superior in the curability, adhesiveness, transparency in the ultraviolet light region and rigidity, and therefore, is useful, as a starting material for a polymerization composition, a cross-linking agent, and various synthetic reagents. Therefore, the 1,1-bis[(ethenyloxy)methyl]cyclohexane of the present invention can be utilized for inks, paints, resists, color filters, adhesives, platemaking materials, sealants, image forming agents, and other applications.

Solution to Problem

In accordance with the present invention, there is provided 1,1-bis[(ethenyloxy)methyl]cyclohexane expressed by the formula (I):

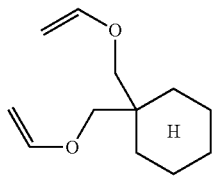

(I)

In accordance with the present invention, there is provided a method for producing 1,1-bis[(ethenyloxy)methyl]cyclohexane expressed by the following formula (I):

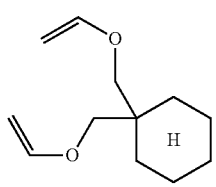

(I)

comprising reacting 1,1-cyclohexanedimethanol expressed by the formula (II):

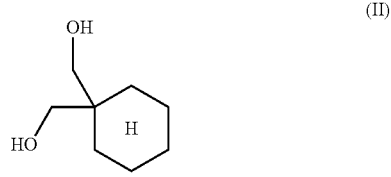

(II)

and acetylene in an aprotic polar solvent.

Advantageous Effects of Invention

The compound 1,1-bis[(ethenyloxy)methyl]cyclohexane according to the present invention is low in odor, low in volatility and low in skin irritability and is expected as having useful properties as a starting material for a polymerization composition having a low toxicity and excellent curability, adhesiveness and transparency in the ultraviolet light region. Further, the present compound has two vinyl ether groups which have special reactivity alone or with another compound at specific positions.

MODE FOR CARRYING OUT THE INVENTION

Figure 1:
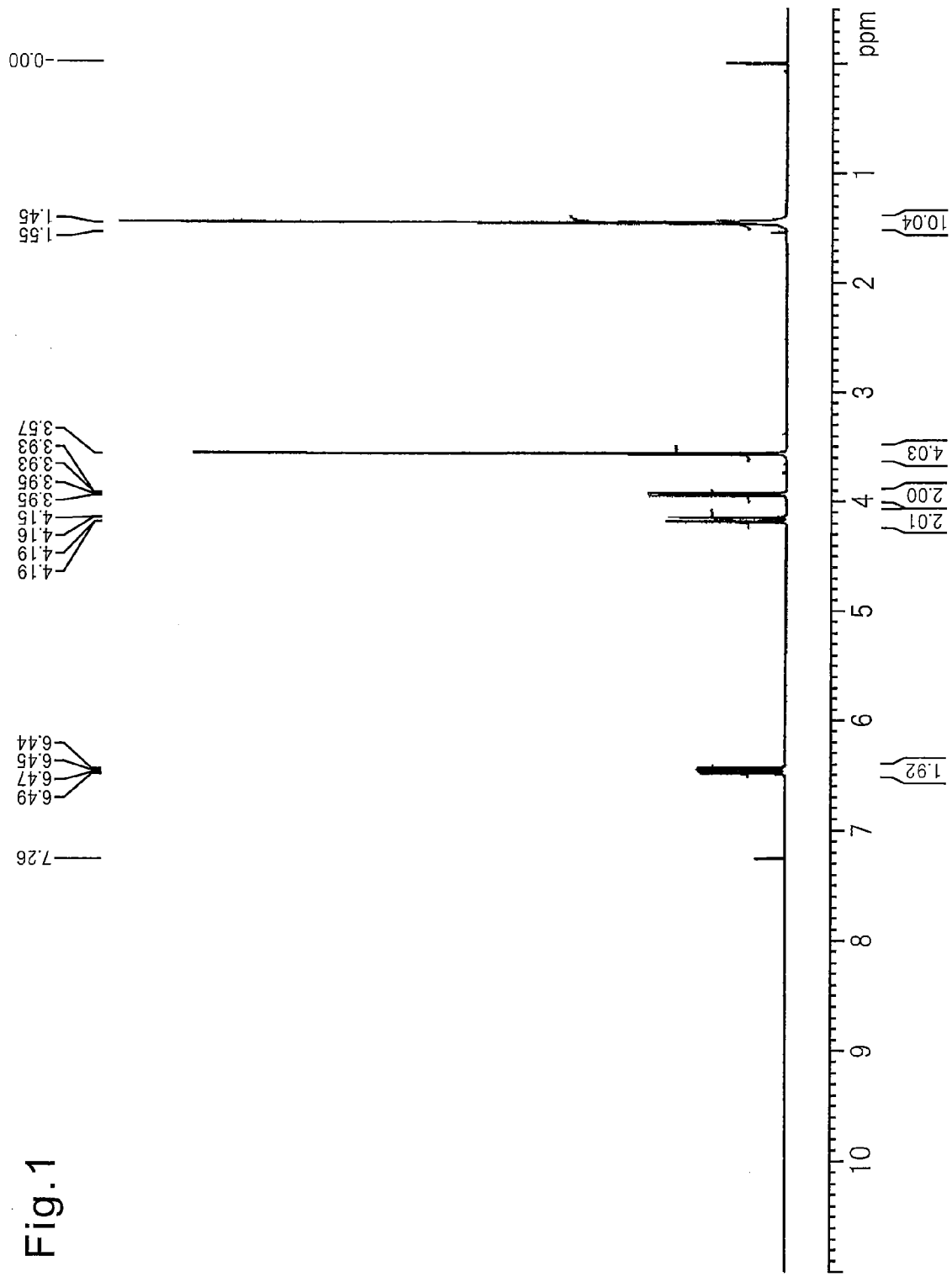
FIG. 1 is an $^1$H-NMR chart of the 1,1-bis[(ethenyloxy)methyl]cyclohexane produced in Example 1.
Figure 2:
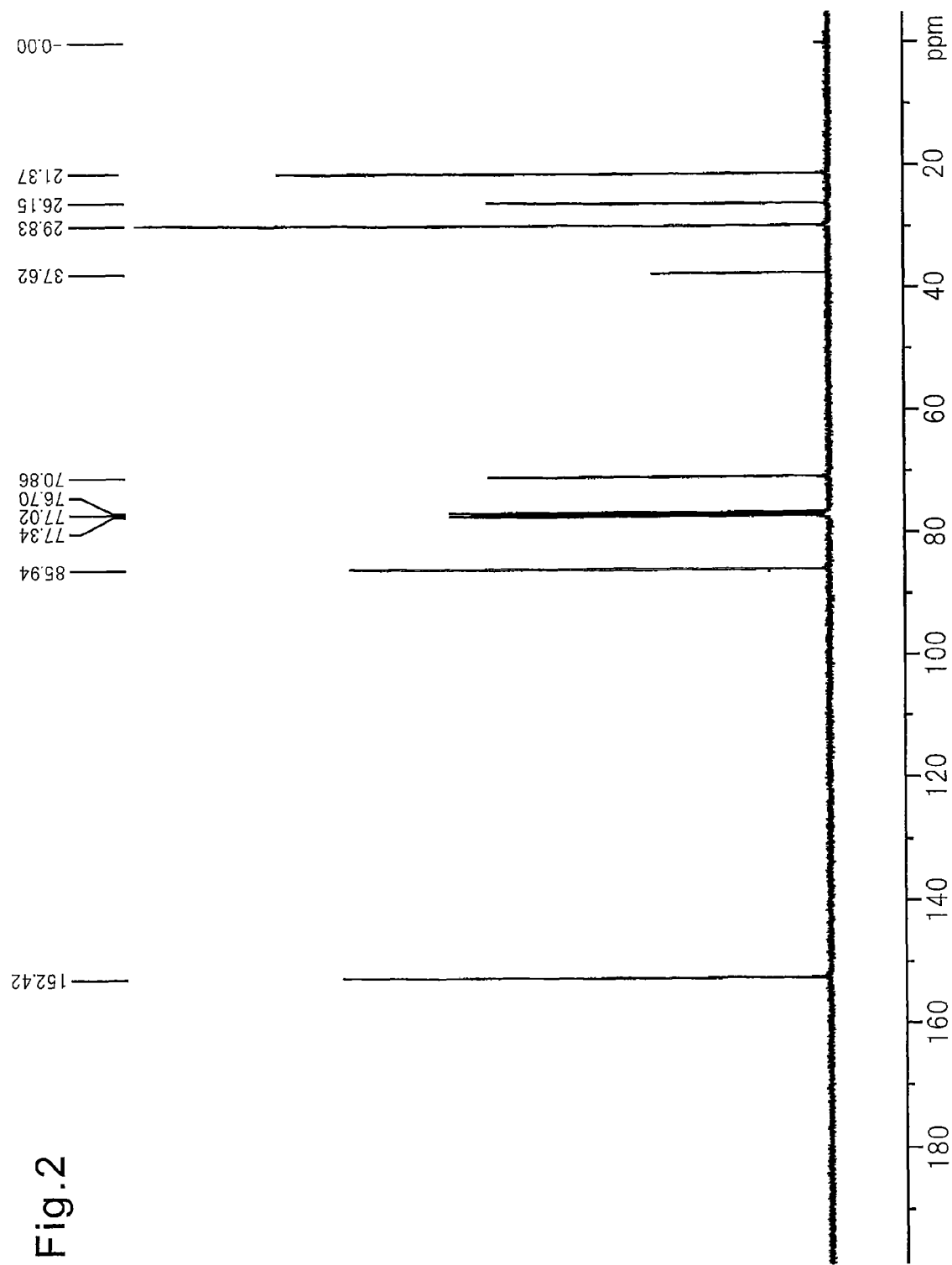
FIG. 2 is a $^{13}$C-NMR chart of the 1,1-bis[(ethenyloxy)methyl]cyclohexane produced in Example 1.

The present invention will now be explained in further detail.

The vinyl ether (I) according to the present invention can be produced in accordance with the following reaction formula:

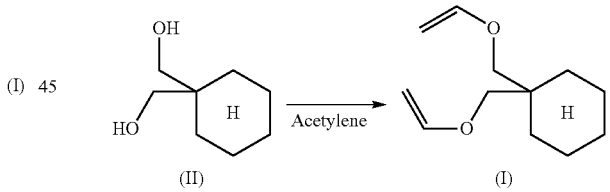

As a specific method for the synthesis of the present compound, for example, the following method may be mentioned.

Inside of a reaction vessel such as an SUS (stainless steel) pressure resistant reaction vessel, as a solvent, an aprotic polar solvent, for example, one or more of a solvent selected from, dimethyl sulfoxide, N-methylpyrrolidone, N,N'-dimethylethylene urea, N,N'-dimethylpropylene urea, N,N'-diethylethylene urea, N,N'-diisopropylethylene urea, N,N,N',N',N'',N''-hexamethyl phosphoric triamide, 1,3,4-trimethyl-2-imidazolidinone, diethylene glycol dimethyl ether, triethylene glycol dimethyl ether, tetraethylene glycol dimethyl ether, and polyethylene glycol dimethyl ether is introduced. Then, the starting compound, 1,1-cyclohexane dimethanol is fed. As a reaction catalyst, an alkaline compound, for example, an alkali metal hydroxide such as potassium hydroxide, sodium hydroxide is added. At this time, the use amount of the aprotic polar solvent is not particularly limited, but the use amount of the aprotic polar solvent is, preferably 100 to 1,000 parts by weight, more preferably 200 to 700 parts by weight, based upon 100 parts by weight of 1,1-cyclohexane dimethanol. If the use amount of the aprotic polar solvent is less than 100 parts by weight, based upon 100 parts by weight of 1,1-cyclohexane dimethanol, the selectivity of the reaction is sometimes decreased, and therefore, this is not preferable. On the other hand, if the use amount of the aprotic polar solvent is more than 1000 parts by weight, based upon 100 parts by weight of 1,1-cyclohexane dimethanol, the removal of the solvent after the end of reaction becomes troublesome, and therefore, this is not preferable. Further, the use amount of the reaction catalyst, that is, alkali compound, is not particularly limited, either. However, the use amount of the alkali compound is preferably at least 2 parts by weight, more preferably 4 to 50 parts by weight, 100 parts by weight of 1,1-cyclohexane dimethanol.

According to the present invention, next, an inert gas such as nitrogen gas may be used to replace the inside of the reaction vessel, then the reaction vessel is sealed and acetylene is added under pressure, while increasing the temperature for causing a reaction, whereby the compound according to the present invention, that is, 1,1-bis[(ethenyloxy)methyl]cyclohexane, can be produced. The atmosphere inside of the reaction vessel may be made acetylene alone, but together with the acetylene, nitrogen, helium, argon, or another inert gas may be used.

As the reaction conditions for producing the 1,1-bis[(ethenyloxy)methyl]cyclohexane according to the present invention, for example, the pressure of the acetylene is preferably, by gauge pressure, 0.01 MPa or more. From the viewpoints of the productivity, the suppression of side reactions, and safety, more preferably the acetylene pressure is by gauge pressure 0.15 MPa to 1.0 MPa. On the other hand, the reaction temperature is 80 to 180° C., preferably 80 to 140° C. From the viewpoint of the reaction velocity, 100° C. or more is preferable. From the viewpoint of economy and suppression of side reactions, the temperature is preferably 130° C. or less.

Note that the starting material of the present compound, that is, 1,1-cyclohexane dimethanol (II), can be produced by a conventionally known method. For example, it may be produced by the method described in WO 2005/005456A.

EXAMPLES

Production Example 1

A 2000 ml volume four-necked flask equipped with a stirrer and a thermometer was charged with 200 ml of tetrahydrofuran and 1300 ml (about 2.0 mol/liter, about 2.6 mol) lithium diisopropylamide solution which was then cooled under an argon atmosphere to −70° C. Under stirring, a mixture of methyl cyclohexanecarboxylate (100.3 g, 0.691 mol) and tetrahydrofuran 100 ml was dropwise added over 1 hour 30 minutes, while holding the temperature of the reaction mixture at −70° C. or less. The mixture was stirred at a temperature of −70° C. or less for about 2 hour 30 minutes. Next, to the reaction solution thus obtained, a mixture of methyl chlorocarbonate (100.0 g, 1.04 mol) and 250 ml of tetrahydrofuran was dropwise added over 3 hours at the same temperature. The resultant mixture was allowed to react at −78° C. to room temperature overnight. Thereafter, the solvent in the reaction vessel was distilled off in vacuo, the residue was charged into 1000 ml of an aqueous saturated ammonium chloride solution and extracted with ethyl acetate, the organic layer was rinsed, then the layer was dried with anhydrous magnesium sulfate. The desiccant (or drying agent) was filtered off and the solvent was distilled off in vacuo to obtain 215.4 g of the reaction mixture. Next, another 3000 ml four-necked flask was charged with 900 ml of tetrahydrofuran and 600 ml of lithium aluminum hydride solution (about 2.0 mol/liter, about 1.2 mol) which were cooled under an argon atmosphere to 0° C. Under stirring, a mixture of 160.2 g of the reaction mixture obtained above and 400 ml of tetrahydrofuran was dropwise added over about 2 hours, while being held at 0° C. or less. The resultant mixture was allowed to stand overnight at 0° C. or less, while stirring. Thereafter, water was dropwise added to this reaction solution and the reaction solution was neutralized with about 6 N hydrochloric acid, then the insoluble salts were filtered off from the reaction solution and the resultant solution was concentrated in vacuo. Subsequently, the residue was charged into 1000 ml of water, was extracted with ethyl acetate, and was dried with anhydrous magnesium sulfate. The desiccant (or drying agent) was removed by filtration, the solvent was distilled off in vacuo, then the residue was charged into n-hexane. The precipitated crystal was repeatedly decanted with n-hexane, then washed, then dried in vacuo to obtain 20.8 g of crystalline powder. This crystalline powder, as a result of analysis by NMR, was 1,1-cyclohexane dimethanol (purity 99.1% by gas chromatography).

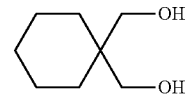

The results of the NMR measurement of the 1,1-cyclohexane dimethanol thus obtained were as follows:
$^1$H-NMR (CDCl$_3$, TMS, 400 MHz): δ ppm 1.34-1.36 (m, 4H), 1.43-1.47 (m, 6H), 2.54 (s, 2H), 3.62 (s, 4H)
$^{13}$C-NMR (CDCl$_3$, 100 MHz): δ ppm 21.4, 26.5, 29.6, 38.3, 70.4

Example 1

A 300 ml SUS pressure resistant reaction vessel equipped with a stirrer, pressure gauge, thermometer, gas introduction tube and gas purge line was charged with 102.2 g of dimethyl sulfoxide, 15.2 g (0.10 mol) of 99.1% purity 1,1-cyclohexane dimethanol obtained in the Production Example 1 and 2.14 g (0.036 mol) of 95.0% purity potassium hydroxide. Under stirring, nitrogen gas was run for about 60 minutes to replace the inside of the container with nitrogen. Next, the reaction vessel was sealed and the vessel was charged with acetylene gas under a pressure of 1.8 kg/cm$^2$. Next, the temperature was gradually raised, while holding the gauge pressure at 1.8 kg/cm$^2$. Control was performed so that the inside temperature of the reaction vessel did not exceed 100° C. The reaction was carried out for about 2 hour 30 minutes. During this time, acetylene gas was sequentially filled to maintain the inside pressure of the reaction vessel constantly at 1.8 kg/cm$^2$. After the end of reaction, the residual acetylene gas was purged to obtain 118.8 g of the reaction solution. As a result of gas chromatography of the reaction solution, the conversion of the 1,1-cyclohexane dimethanol quantitatively proceeded. The selectivity of the desired 1,1-bis[(ethenyloxy) methyl] cyclohexane was 98.2%.

Next, the reaction solvent was removed from the reaction solution, then the solution was distilled in vacuo (0.2 kPa) to collect the fraction obtained at 75° C. to 76° C. in 16.9 g. The fraction thus obtained was analyzed by NMR. As a result, the fraction was 1,1-bis[(ethenyloxy) methyl]cyclohexane of the following formula (purity 98.9% by gas chromatography, yield 81.5%).

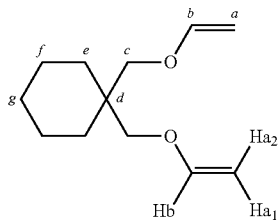

The results of the NMR measurement of the 1,1-bis[(ethenyloxy)methyl]cyclohexane thus obtained are shown below:

$^1$H-NMR (CDCl$_3$, TMS, 400 MHz): δ ppm 1.45 (s, 10H; e, f, g), 3.57 (s, 4H; c), 3.94 (dd, 2H, J=6.8, 1.9 Hz; Ha$_1$), 4.17 (dd, 2H, J=14.3, 1.9 Hz; Ha$_2$), 6.46 (dd, 2H, J=14.3, 6.8 Hz; Hb)

$^{13}$C-NMR (CDCl$_3$, 100 MHz): δ ppm 21.4 (e or f), 26.2 (g), 29.8 (e or f), 37.6 (d), 70.9 (c), 85.9 (a), 152.4 (b)

Application Example 1

The 1,1-bis[(ethenyloxy)methyl]cyclohexane obtained in Example 1 was used for polymerization as follows:

As a polymerization initiator and Lewis acid, HCl/ZnCl$_2$ was used. To a Schlenk flask 4.0 ml of the 1,1-bis[(ethenyloxy)methyl]cyclohexane solution, 0.5 ml of 0.18% HCl solution and 0.5 ml of a ZnCl$_2$ solution were injected in this order by a syringe to start the polymerization. The polymerization was carried out in methylene chloride at −30° C., in the monomer concentration of 0.15 mol/liter, a HCl concentration of 5.0 mmol/liter and a ZnCl$_2$ concentration of 2.0 mmol/liter. The polymerization was stopped at 20 minutes when the polymerization rate reached 100% by adding methanol containing a small among of an aqueous ammonia to the polymerization system.

The solution after the polymerization was stopped was transferred to a separatory funnel, diluted with methylene chloride, and washed three times with an aqueous sodium chloride saturated solution. Next, the solvent was removed from the organic layer by an evaporator and the layer was dried in vacuo to obtain the product polymer.

This polymer was decanted with methanol to be further purified. The number average molecular weight $M_n$ of the polymer thus obtained was 3800 and the molecular weight distribution $M_w/M_n$ was 1.65.

The divinyl ether homopolymer obtained in Application Example 1 was used for a material for ink use, whereupon low odor, low volatility, low skin irritability, and low in toxicity were confirmed and, further, high glass transition temperature was confirmed. Thus, superior performance was exhibited.

The divinyl ether homopolymer obtained in Application Example 1 was used for a material for electronic material use, whereupon low odor, low volatility, low skin irritability and low toxicity were confirmed and, further, a high glass transition temperature was confirmed. Thus superior performance was exhibited.

INDUSTRIAL APPLICABILITY

The 1,1-bis[(ethenyloxy)methyl]cyclohexane of the present invention is polymerized to form a divinylether homopolymer, which exhibits the excellent performance of a high glass transition temperature and, further, is excellent in the curability, substrate adhesiveness and transparency and also is excellent in the heat resistance, and therefore, is useful for a starting material for ink application such as ink and paint and starting materials for electronic materials such as resists, color filters, adhesives, platemaking materials, sealants and image formation, etc.

The invention claimed is:
1. 1,1-bis[(ethenyloxy)methyl]cyclohexane expressed by the formula (I):

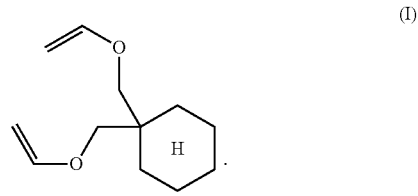

(I)

2. A method for producing 1,1-bis[(ethenyloxy)methyl]cyclohexane expressed by the formula (I):

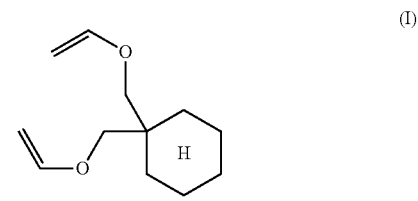

(I)

comprising reacting 1,1-cyclohexane dimethanol expressed by the formula (II):

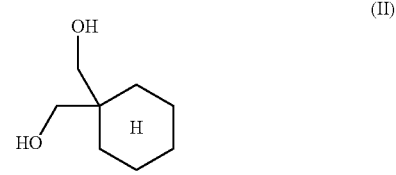

(II)

and acetylene to react in an aprotic polar solvent.

3. The method as claimed in claim 2, wherein said aprotic polar solvent is selected from dimethyl sulfoxide, N-methylpyrrolidone, N,N'-dimethylethylene urea, N,N'-dimethylpropylene urea, N,N'-diethylethylene urea, N,N'-diisopropylethylene urea, N,N,N',N',N'',N''-hexamethylphosphoric triamide, 1,3,4-trimethyl-2-imidazolidinone, diethylene glycol dimethyl ether, triethylene glycol dimethyl ether, tetraethylene glycol dimethyl ether and polyethylene glycol dimethyl ether.

4. The method as claimed in claim 2, wherein said reaction is carried out at a temperature of 80° C. to 180° C. and an acetylene pressure (gauge pressure) of 0.01 MPa or more.

5. The method as claimed in claim 3, wherein said reaction is carried out at a temperature of 80° C. to 180° C. and an acetylene pressure (gauge pressure) of 0.01 MPa or more.

* * * * *